(12) United States Patent
Nonomura et al.

(10) Patent No.: US 9,265,730 B2
(45) Date of Patent: *Feb. 23, 2016

(54) STABLE SOLID PREPARATIONS

(71) Applicant: TAKEDA PHARMACEUTICAL COMPANY LIMITED, Osaka-shi, Osaka (JP)

(72) Inventors: Muneo Nonomura, Osaka (JP); Hiroki Ito, Suita (JP); Hideo Hashimoto, Osaka (JP); Tadashi Urai, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/194,050

(22) Filed: Feb. 28, 2014

(65) Prior Publication Data

US 2014/0205670 A1    Jul. 24, 2014

Related U.S. Application Data

(63) Continuation of application No. 10/530,785, filed as application No. PCT/JP03/13152 on Oct. 15, 2003, now Pat. No. 8,697,094.

(30) Foreign Application Priority Data

Oct. 16, 2002    (JP) .................................. 2002-301893

(51) Int. Cl.
*A61K 9/16* (2006.01)
*A61K 9/24* (2006.01)
(Continued)

(52) U.S. Cl.
CPC ............... *A61K 9/1676* (2013.01); *A61K 9/209* (2013.01); *A61K 9/4808* (2013.01); *A61K 31/4439* (2013.01); *A61K 47/02* (2013.01)

(58) Field of Classification Search
CPC . A61K 31/4439; A61K 47/02; A61K 9/1676; A61K 9/209; A61K 9/4808
See application file for complete search history.

(56) References Cited

U.S. PATENT DOCUMENTS 4,628,098 A    12/1986    Nohara et al.
4,853,230 A    8/1989    Lovgren et al.
(Continued)

FOREIGN PATENT DOCUMENTS

CN    1329003    1/2002
DE    40 35 455    5/1992
(Continued)

OTHER PUBLICATIONS

Nagaya et al. "Effects of the Enantiomers of Lansoprazole (AG-1749) on (H+ +K+)-ATPase Activity in Canine Gastric Microsomes and Acid Formation in Isolated Canine Parietal Cells". *Biochemical Pharmacology*, vol. 42. No. 10, pp. 1875-1878 (1991).
(Continued)

*Primary Examiner* — Aradhana Sasan
(74) *Attorney, Agent, or Firm* — Hamre, Schumann, Mueller & Larson, P.C.

(57) ABSTRACT

It is intended to provide a process for producing unstable amorphous benzimidazole compounds having a proton pump inhibitor function, and stable solid preparations for medicinal use containing these compounds which are produced by blending such an amorphous benzimidazole compound with a nontoxic base such as a basic inorganic salt, forming an intermediate coating layer on the layer containing the active ingredient and further forming an enteric coating layer or a release-controlling coating layer.

21 Claims, 4 Drawing Sheets

(51) Int. Cl.
*A61K 9/48* (2006.01)
*A61K 31/4439* (2006.01)
*A61K 47/02* (2006.01)

(56) References Cited

U.S. PATENT DOCUMENTS

| | | | |
|---|---|---|---|
| 5,260,068 | A | 11/1993 | Chen |
| 5,476,669 | A | 12/1995 | Borody |
| 5,578,732 | A | 11/1996 | Kato et al. |
| 5,656,290 | A | 8/1997 | Kelm et al. |
| 5,861,142 | A | 1/1999 | Schick |
| 5,879,708 | A | 3/1999 | Makino et al. |
| 5,948,789 | A | 9/1999 | Larsson et al. |
| 6,110,494 | A | 8/2000 | Clancy et al. |
| 6,274,173 | B1 | 8/2001 | Sachs et al. |
| 6,328,994 | B1 | 12/2001 | Shimizu et al. |
| 6,369,085 | B1 | 4/2002 | Cotton et al. |
| 6,378,518 | B1 | 4/2002 | Miekka et al. |
| 6,379,705 | B1 | 4/2002 | Mendes et al. |
| 6,462,058 | B1 | 10/2002 | Fujishima et al. |
| 6,635,280 | B2 | 10/2003 | Shell et al. |
| 6,664,276 | B2 | 12/2003 | Fujishima et al. |
| 6,780,436 | B1 | 8/2004 | Lopez-Cabrera et al. |
| 6,897,205 | B2 | 5/2005 | Beckert et al. |
| 6,939,971 | B2 | 9/2005 | Fujishima et al. |
| 7,285,668 | B2 | 10/2007 | Hashimoto et al. |
| 8,697,097 | B2 * | 4/2014 | Nonomura et al. ........... 424/400 |
| 2002/0034541 | A1 | 3/2002 | Valducci |
| 2002/0042433 | A1 | 4/2002 | Yelle et al. |
| 2002/0045646 | A1 | 4/2002 | Phillips |
| 2003/0008903 | A1 | 1/2003 | Barberich et al. |
| 2003/0171591 | A1 | 9/2003 | Hashimoto et al. |
| 2004/0006111 | A1 | 1/2004 | Widder et al. |
| 2004/0010151 | A1 | 1/2004 | Finkelstein et al. |
| 2007/0004779 | A1 | 1/2007 | Hashimoto et al. |
| 2011/0020410 | A1 | 1/2011 | Nonomura et al. |

FOREIGN PATENT DOCUMENTS

| | | |
|---|---|---|
| EP | 0 224 249 | 6/1987 |
| EP | 0 237 200 | 9/1987 |
| EP | 0 248 634 | 12/1987 |
| EP | 0 277 741 | 8/1988 |
| EP | 0 423 748 | 4/1991 |
| EP | 0 496 437 | 7/1992 |
| EP | 0 694 547 | 1/1996 |
| EP | 1 004 305 | 5/2000 |
| EP | 1 191 025 | 3/2002 |
| EP | 1 405 621 | 4/2004 |
| EP | 1 457 207 | 9/2004 |
| JP | 62-258320 | 11/1987 |
| JP | 62-277322 | 12/1987 |
| JP | 5-255088 | 10/1993 |
| JP | 11-501950 | 2/1999 |
| JP | 11-322605 | 11/1999 |
| JP | 2000-355540 | 12/2000 |
| JP | 2001-39975 | 2/2001 |
| JP | 2001-58990 | 3/2001 |
| JP | 2001-72675 | 3/2001 |
| JP | 2001-509791 | 7/2001 |
| JP | 2003-246733 | 9/2003 |
| WO | WO 94/27988 | 12/1994 |
| WO | WO 96/01622 | 1/1996 |
| WO | WO 96/02535 A1 | 2/1996 |
| WO | WO 96/02535 C1 | 2/1996 |
| WO | WO 96/17077 | 6/1996 |
| WO | WO 97/02261 | 1/1997 |
| WO | WO 98/21201 | 5/1998 |
| WO | WO 98/22118 | 5/1998 |
| WO | WO 98/28294 | 7/1998 |
| WO | WO 99/32091 | 7/1999 |
| WO | WO 99/32093 | 7/1999 |
| WO | WO 99/38512 | 8/1999 |
| WO | WO 99/38513 | 8/1999 |
| WO | WO 99/56698 | 11/1999 |
| WO | WO 00/06126 | 2/2000 |
| WO | WO 00/08017 | 2/2000 |
| WO | WO 00/78745 | 12/2000 |
| WO | WO 01/36409 | 5/2001 |
| WO | WO 02/44167 | 6/2002 |
| WO | WO 02/060415 | 8/2002 |
| WO | WO 03/017980 | 3/2003 |
| WO | WO 03/032953 | 4/2003 |
| WO | WO 03/063840 | 10/2003 |

OTHER PUBLICATIONS

Vrecer. "Investigation at glassy state of two novel benzimidazole derivatives". *Farm Vesin*, vol. 50, pp. 347-348 (1999).

Robinson et al. "Effective Maintenance Treatment of Reflux Esophagitis with Low-Dose Lansoprazole". *Annals of Internal Medicine*. vol. 124, No. 10 (May 15, 1996) 859-867.

Marvola et al. Enteric polymers as binders and coating materials in multiple-unit-site-specific drug delivery systems *European Journal of Pharmaceutical Science*, vol. 7 (1999) 259-267.

Mikawa et al. "Lansoprazole reduces preoperative gastric fluid acidity and volume in children". *Can. J. Anaesth.*, vol. 42, No. 6, (1995) 467-72.

Katsuki et al. "Determination of R(+)- and S(−)-Lansoprazole Using Chiral Stationary-Phase Liquid Chromatography and their Enantioselective Pharmacokinetics in Humans", *Pharmaceutical Research*, vol. 13, No. 4, (1996) 611-615.

Hirschowitz et al. "Long-term treatment with lansoprazole for patients with Xollinger-Ellison syndrome". *Aliment Pharmacol. Ther.*, vol. 10 (1996) 507-522.

Haleblian et al. "Pharmaceutical Applications of Polymorphism". Journal of Pharmaceutical Sciences, vol. 58, No. 8 (Aug. 1969) 911-929.

Gerkensmeier et al. "Sell-Assembly of 2,8,14,20-Tetraisobutyl-5,11,17,23-tetrahydroxyresorc[4]arene", *Eur. J. Org. Chem.* (1999) 2257-2262.

Borner et al. "Separation of Lansoprazole Enantiomers in Human Serum by HPLC", Chromatographia vol. 47, No. 3/4, (Feb. 1998)171-175.

Atwood et al. "Hydrogen-bonded molecular capsules are stable in polar media"., *Chem. Commun.*. (2001) 2376-2377.

Arimori et al. "Pharmacokinetic Differences Between Lansoprazole Enantiomers in Rats", *J. Phann. Pharmacol.*, vol. 50 (1998) 1241-1245.

Brittan. "Methods for the Characterization of Polymorphs and Solvates". *Polymorphism in Pharmaceutical Solids* (1999) 227-278.

American Chemcial Society (Pub). Chemical Abstracts, vol. 127, No. 26, Abstracts 1-28414 (1997) 751-752.

Tietze et al. *Reactions and Synthesis in the Organic Chemistry Laboratory*, (1989) 23-26.

The United States Pharmacopia USP 25, The National Formulary NF20, X-Ray Diffraction, (2002) 2088-2089.

The United States Pharmacopia USP 28, The National Formulary NF23, X-Ray Diffraction (2005) 2513-2514.

The United States Pharmacopia USP 23, The National Formulary NF18, X-Ray Diffraction (1995) 1843-1844.

The United States Pharmacopia USP 32, The National Formulary NF27, Lansoptazole (2009) 2751-2754.

Eagleson. *Concise Encyclopedia Chemistry*, (1993) 872-873.

Rowe et al. (Eds.) *Handbook of Pharmaceutical Excipients Fourth Edition*. (1986) 120-124, 302-305, 462-468, 538-540.

Kotar at al. "Study of polymorphism of a novel antiulcer drug." *European Journal of Pharmaceutical Sciences*, vol. 4, Supplement 1 (1996). 182-182(1).

*Physician's Desk Reference, 55th Edition*, Prevacid®. (2001) 3189-3194.

*Physician's Desk Reference, 51st Edition*, Prevacid®. (1997) 338, 2746-2748.

Gordon et al. *The Chemist's Companion A Handbook of Practical Data, Techniques and References*. (1972) 440-445.

Rouhi. "The Right Stuff From research and development to the clinic, getting drug crystals right is full of pitfalls", *Chemical & Engineering News*, vol. 81, No. 8, (Feb. 2003) 31-35.

(56) References Cited

OTHER PUBLICATIONS

Bauer, "Tharmaceutical Solids—The Amorphous Phase", *Journal of Validation Technology* (*2009*), 63-68.

Kawakami. "Modification of physicochemicai characteristics of active pharmaceutical ingredients and application of supersaturatable dosage forms for improving bioavailability of poorly absorbed drugs". *Advanced Drug Delivery Reviews*, vol. 64 (2012) 480-495.

* cited by examiner

STABLE SOLID PREPARATIONS

This application is a continuation of U.S. Ser. No. 10/530,785 filed 8 Apr. 2005, which is a U.S. National Stage application of International No. PCT/JP03/13152, filed 15 Oct. 2003, which is incorporated herein by reference.

TECHNICAL FIELD

The present invention is directed toward a stable solid preparation for medicinal use containing an amorphous benzimidazole compound, which is useful as a proton pump inhibitor, but unstable to water and the like as well as to acids.

BACKGROUND ART

Since benzimidazole compounds such as lansoprazole, omeprazole, rabeprazole and the like have a proton pump inhibitor (hereinafter, abbreviated as 'PPI') like activity such as gastric acid secretion suppressing effect and gastric mucosa defensive effect, these compounds are used extensively as an agent for treatment of peptic ulcer disease and the like.

However, these compounds, in particular, amorphous benzimidazole compounds have a poor stability, and are unstable not only to temperature, humidity and light but also to water in solid state, which results in a terrible change in color etc. In particular, they are very unstable to acids and become extremely unstable in aqueous solution or suspension as the pH of the solution or suspension decreases.

In addition, as for the stability in a dosage form, namely, tablets, powders, fine granules, capsules, etc., compounds are more unstable than in compounds alone because there are strong interactions with these compounds and other ingredients in the formula of dosage form, and consequently, change in color or degradation is observed during manufacturing and storage. In order to stabilize these compounds, for example, JP-A 62-277322 discloses enteric coating granules or enteric coating fine granules after blending some stabilizers namely, basic inorganic salt of magnesium and/or calcium.

Since benzimidazole compounds having a PPI activity have generally a property of hard to dissolve in water and are unstable in acids, an enteric coating is needed to be applied to them. An enteric coating layer is applied expecting that a benzimidazole compounds are not dissolved in the stomach having a low pH value and comparatively much water, but are dissolved and absorbed in the small intestine having a high pH value and less water. However, a document that discloses specifically about studies on the stabilization of a preparation containing an amorphous benzimidazole compound, which is unstable to atmospheric moisture as well as to acids, has not been reported.

Furthermore, a solution, suspension, tablet and capsule obtained by combining omeprazole or lansoprazole, which is not enteric-coated, with an alkali metal salt of bicarbonate are disclosed in U.S. Pat. No. 5,840,737 and WO 00/26185.

However, since these dosage forms are combination dosage forms with compounds and a bicarbonate, the bicarbonate reacts with gastric acid, and carbon dioxide is generated. This gas causes burping, therefore they are not preferred with a viewpoint of compliance.

DISCLOSURE OF INVENTION

Technical Problems to be Solved by the Invention

An object of the present invention is to provide a stable solid dosage form for medicinal use containing an unstable amorphous benzimidazole compound having a proton pump inhibitor (PPI) activity.

SUMMARY OF THE INVENTION

Namely, the present invention provides:

(1) A stable solid dosage form comprising a non-toxic base and an amorphous benzimidazole compound having a proton pump inhibitor (PPI) activity;

(2) The solid dosage form according to the above-mentioned (1), wherein the benzimidazole compound is an optically active isomer;

(3) The solid dosage form according to the above-mentioned (2), wherein the optically active isomer of benzimidazole compound is a compound represented by the formula (I):

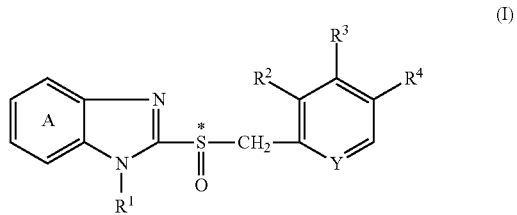

wherein ring A is an optionally substituted benzene ring, $R^1$ is a hydrogen atom, an optionally substituted aralkyl group, acyl group or acyloxy group, $R^2$, $R^3$ and $R^4$ are the same or different and each represent a hydrogen atom, an optionally substituted alkyl group, an optionally substituted alkoxy group or an optionally substituted amino group, Y represents a nitrogen atom or CH, and * represents asymmetric center, or a salt thereof;

(4) The solid dosage form according to the above-mentioned (2), wherein the optically active isomer of benzimidazole compound is an optically active isomer of lansoprazole, omeprazole, rabeprazole or pantoprazole;

(5) The solid dosage form according to the above-mentioned (2), wherein the optically active isomer of benzimidazole compound is an optically active isomer of lansoprazole;

(6) The solid dosage form according to the above-mentioned (5), wherein the optically active isomer of lansoprazole is R-isomer;

(7) The solid dosage form according to the above-mentioned (5), wherein the optically active isomer of lansoprazole is S-isomer;

(8) The solid dosage form according to the above-mentioned (1), wherein the non-toxic base is an inorganic salt of which 1% aqueous solution or 1% aqueous suspension shows a pH value of 8.0 or more at 25° C.;

(9) The solid dosage form according to the above-mentioned (1), wherein the non-toxic base is one or more basic inorganic salt selected from the group consisting of magnesium carbonate, calcium carbonate, magnesium hydroxide, magnesium oxide, sodium carbonate, sodium bicarbonate and sodium hydroxide;

(10) The solid dosage form according to the above-mentioned (1), which has a coating layer;

(11) The solid dosage form according to the above-mentioned (10), wherein the coating layer contains an enteric coating layer;

(12) The solid dosage form according to the above-mentioned (10), wherein the coating layer contains a controlled release coating later;

(13) The solid dosage form according to the above-mentioned (10), wherein the coating layer contains an intermediate coating layer formed on a layer containing an amorphous benzimidazole compound and a controlled release coating later and/or enteric coating layer formed on said intermediate coating layer;

(14) The solid dosage form according to the above-mentioned (1), wherein the non-toxic base contains at least one component selected from metal oxides and at least one component selected from metal hydroxides;

(15) The solid dosage form according to the above-mentioned (14), which is gastric disintegrable;

(16) The solid dosage form according to the above-mentioned (14), which comprises at least one metal oxide selected from the group consisting of magnesium oxide, magnesium silicate, dry aluminum hydroxide gel and magnesium metasilicate aluminate;

(17) The solid dosage form according to the above-mentioned (14), which comprises at least one metal hydroxide selected from the group consisting of magnesium hydroxide, aluminum hydroxide, synthetic Hydrotalcite, coprecipitate of aluminum hydroxide and magnesium hydroxide, coprecipitate of aluminum hydroxide, magnesium carbonate and calcium carbonate, and coprecipitate of aluminum hydroxide and sodium bicarbonate;

(18) The solid dosage form according to the above-mentioned (14), which comprises further a basic inorganic salt stabilizer with a carbonate of alkaline earth metal;

(19) A stabilized solid dosage form which comprises a layer containing an amorphous optically active R-isomer of lansoprazole and at least one basic inorganic salt selected from the group consisting of magnesium carbonate, calcium carbonate, magnesium hydroxide, magnesium oxide, sodium carbonate, sodium bicarbonate and sodium hydroxide, an intermediate coating layer formed on said layer, and an enteric coating layer formed on said intermediate coating layer;

(20) The solid dosage form according to the above-mentioned (19), wherein the basic inorganic salt is magnesium carbonate or calcium carbonate;

(21) A process for manufacturing a stable solid dosage form containing an amorphous benzimidazole compound having a PPI activity, which is packed in the packaging configuration selected from the group consisting of oxygen permeation inhibitory packaging, gas exchanged packaging, vacuum packaging and deoxidant-encapsulated packaging;

(22) The manufacturing process according to the above-mentioned (21), wherein a non-toxic base is compounded:

(23) A process for producing an amorphous optically active isomer of lansoprazole which comprises keeping hydrated crystals of optically active isomer (R-isomer) of lansoprazole at about 20 to about 100° C.;

(24) The process for producing an amorphous optically active isomer of lansoprazole according to the above-mentioned (23), which comprises heating at about 40 to about 80° C.;

(25) The process according to the above-mentioned (23), wherein 0.5 to 1.5 hydrate crystals of optically active isomer (R-isomer) of lansoprazole is heated at about 50 to about 70° C.; and

(26) The process according to the above-mentioned (23), wherein the keeping of the temperature is carried out under reduced pressure or under ventilation.

BEST MODE FOR CARRYING OUT THE INVENTION

Figure 1:
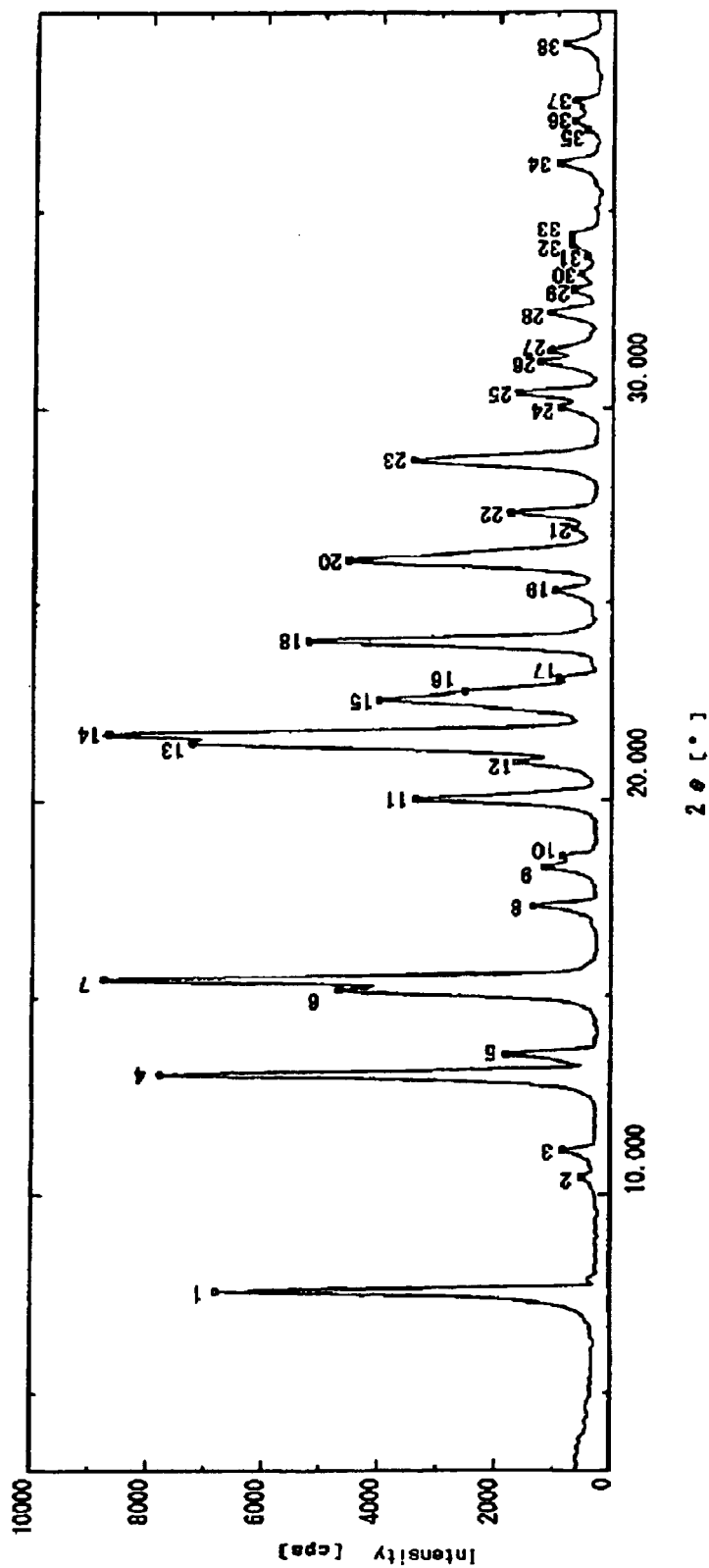
FIG. 1 is a powder X-ray chart for crystals of lansoprazole R-isomer anhydride.
Figure 2:
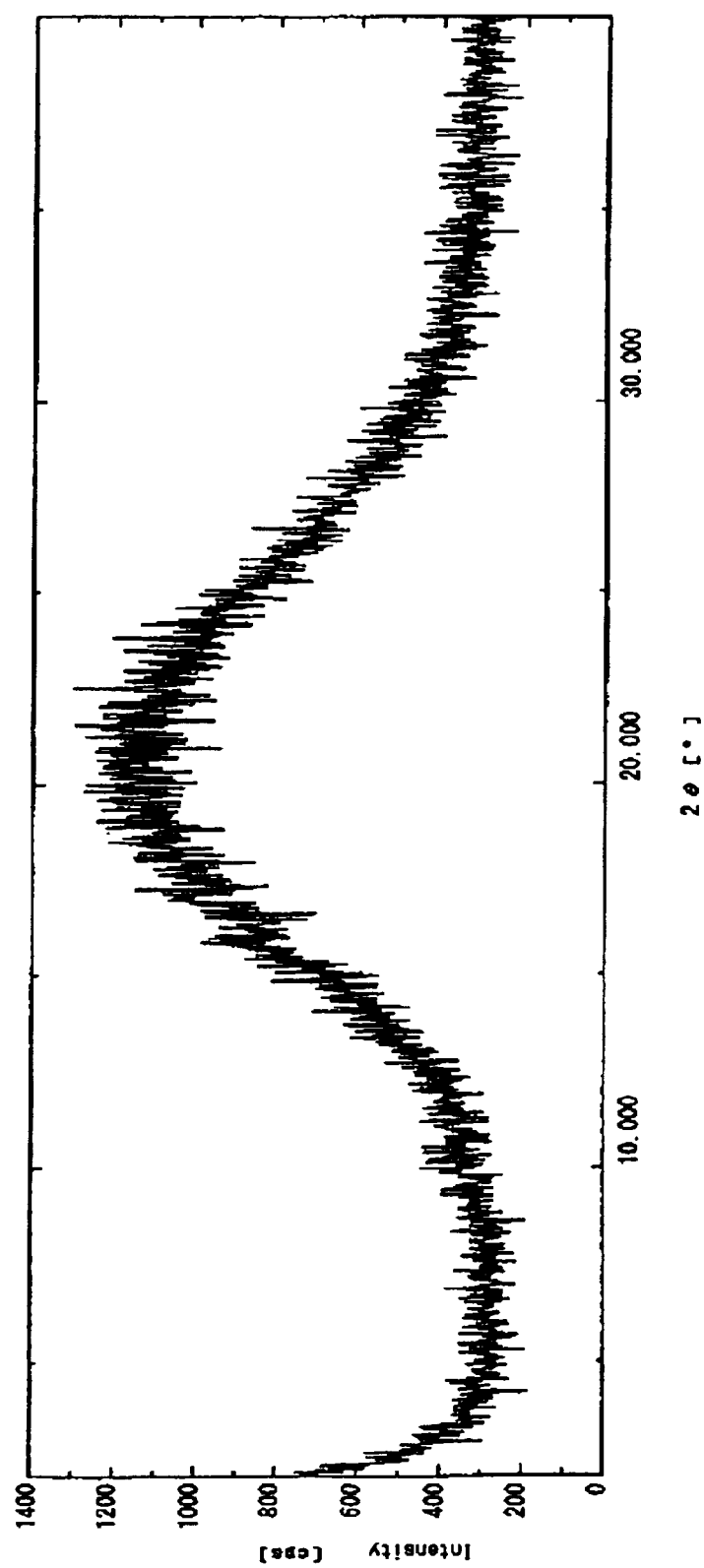
FIG. 2 is a powder X-ray diffraction chart exhibiting an amorphous form for Production Example 1.
Figure 3:
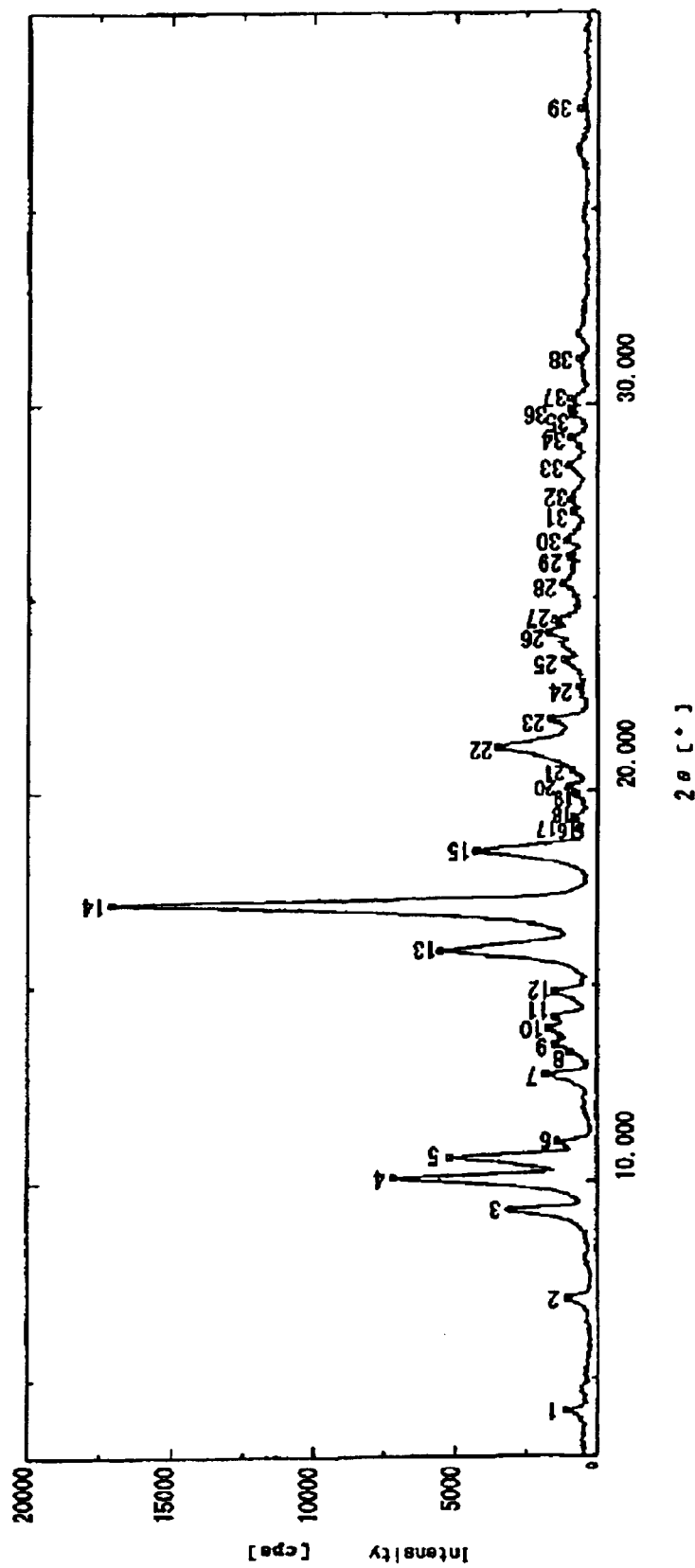
FIG. 3 is a powder X-ray chart exhibiting lansoprazole R-isomer 0.5 hydrate of Reference Example 1.
Figure 4:
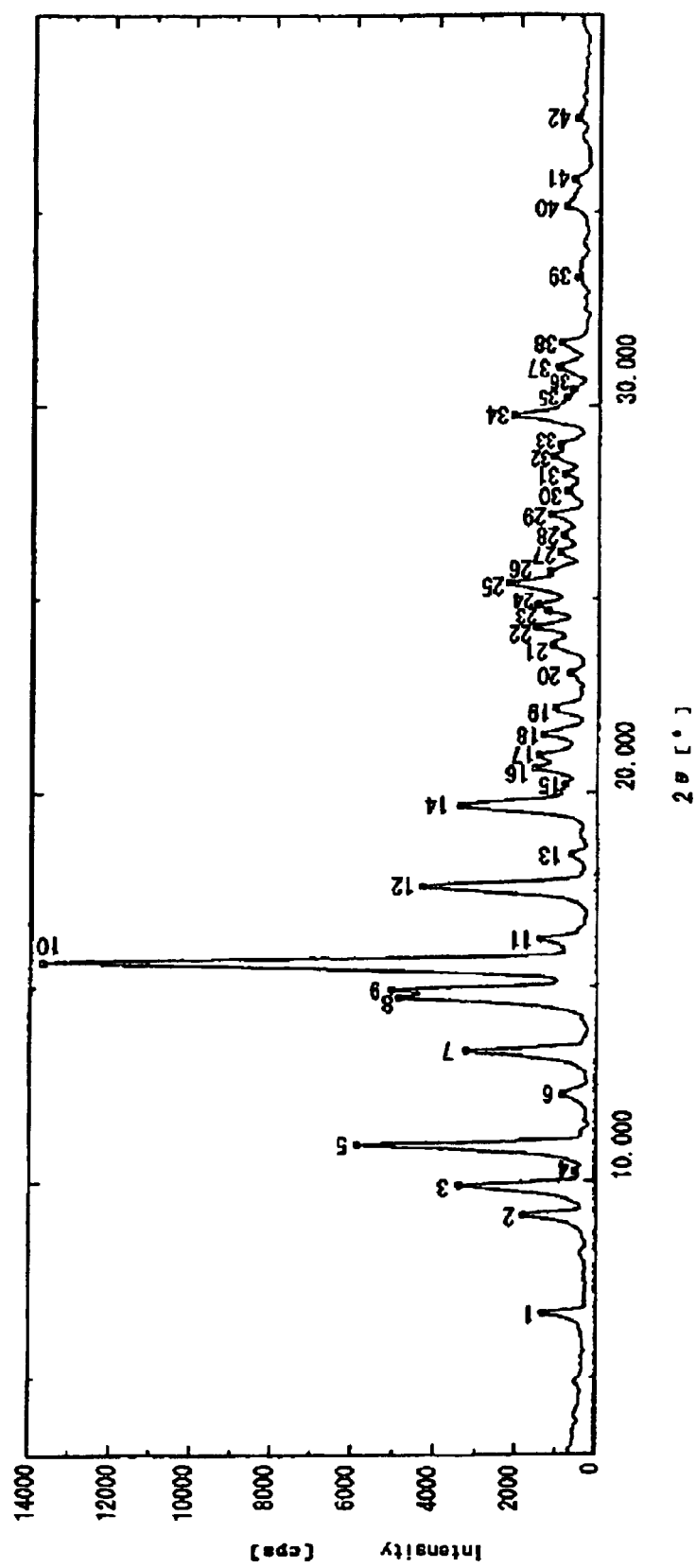
FIG. 4 is a powder X-ray chart exhibiting lansoprazole R-isomer 1.5 hydrate of Reference Example 2.

The solid dosage form of the present invention is a solid dosage form which stabilized amorphous benzimidazole compounds having a PPI activity represented by the above formula (I), which are unstable active ingredients, in particular, extremely unstable in acid, by blending with a non-toxic base, preferably a basic inorganic salt, furthermore by forming an enteric coating layer and/or a controlled release coating layer on the core particle containing these active ingredients, and if necessary, by forming an intermediate coating layer in order to prevent a direct contact of the particles with these coating layer. Here, in the present specification, the 'enteric coating layer' means a usual coating layer which is dissolved at a pH of about 5.5, and the 'controlled release coating layer' does not include above mentioned usual enteric coating layer, and means a pH-dependent coating layer that is dissolved at a different pH region from that of usual enteric coating layer or a diffusion-controlled coating layer which releases an active ingredient through pores formed in the coating layer although said coat itself is not dissolved.

As the benzimidazole compound having a PPI activity used in the present invention, preferred is a compound represented by the following formula (I'):

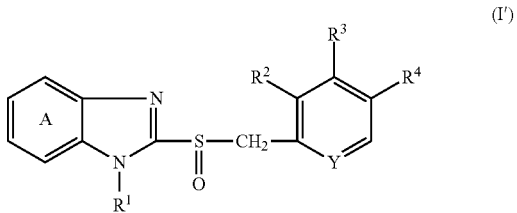

wherein ring A represents an optionally substituted benzene ring, $R^1$ represents a hydrogen atom, an optionally substituted aralkyl group, an acyl group or an acyloxy group, $R^2$, $R^3$ and $R^4$ are the same or different and each represent a hydrogen atom, an optionally substituted alkyl group, an optionally substituted alkoxy group or an optionally substituted amino group, and Y represents a nitrogen atom or CH, or an optically active isomer thereof or a salt thereof. Among them, the optically active isomers represented by the above formula (I) or a salt thereof are preferred as a medicine. Although these compounds are unstable in an amorphous form as mentioned above, and decompose and discolor significantly by itself, it was found that they are stabilized unexpectedly by making into a dosage form and are useful as a medicine.

In the above-mentioned formula (I') and (I), the preferable compound is a compound wherein ring A is a benzene ring which may have a substituent selected from a halogen atom, an optionally halogenated $C_{1-4}$ alkyl group, an optionally halogenated $C_{1-4}$ alkoxy group and a 5- or 6-membered heterocyclic group, $R^1$ is a hydrogen atom, $R^2$ is a $C_{1-6}$ alkyl group, a $C_{1-6}$ alkoxy group, a $C_{1-6}$ alkoxy-$C_{1-6}$ alkoxy group or a di-$C_{1-6}$ alkylamino group, $R^3$ is a hydrogen atom, a $C_{1-6}$ alkoxy-$C_{1-6}$ alkoxy group or an optionally halogenated $C_{1-6}$ alkoxy group, $R^4$ is a hydrogen atom or a $C_{1-6}$ alkyl group, and Y is a nitrogen atom, or a salt thereof.

Particularly preferred is a compound represented by the formula (Ia):

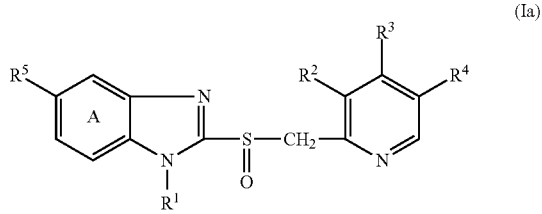

(Ia)

wherein $R^1$ represents a hydrogen atom, $R^2$ represents a $C_{1-3}$ alkyl group or a $C_{1-3}$ alkoxy group, $R^3$ represents a $C_{1-3}$ alkoxy group which is halogenated or substituted with a $C_{1-3}$ alkoxy group, $R^4$ represents a hydrogen atom or a $C_{1-3}$ alkyl group, and $R^5$ represents a hydrogen atom, an optionally halogenated $C_{1-3}$ alkoxy group or a pyrrolyl group (for example, 1-, 2- or 3-pyrrolyl group), or an optically active isomer thereof or a salt thereof.

In the formula (Ia), the compound wherein $R^1$ is a hydrogen atom, $R^2$ is a $C_{1-3}$ alkyl group, $R^3$ is an optionally halogenated $C_{1-3}$ alkoxy group, $R^4$ is a hydrogen atom and $R^5$ is a hydrogen atom or an optionally halogenated $C_{1-3}$ alkoxy group, or an optically active isomer thereof or a salt thereof is particularly preferred.

In the compound represented by the above-mentioned formula (I') [hereinafter, referred to as compound (I'); compound (I') includes the compounds represented by the formula (I) or formula (Ia) and optically active isomers thereof, namely, compound (I), compound (Ia) and optically active isomers thereof, and hereinafter collectively referred to as compound (I')], the "substituent" for the "optionally substituted benzene ring" represented by ring A includes, for example, a halogen atom, a cyano group, a nitro group, an optionally substituted alkyl group, a hydroxy group, an optionally substituted alkoxy group, an aryl group, an aryloxy group, a carboxy group, an acyl group, an acyloxy group, a 5- to 10-membered heterocyclic ring group and the like. The benzene ring may be substituted with about 1 to 3 of these substituents. When the number of substituents is 2 or more, each substituents may be the same or different. Among these substituents, a halogen atom, an optionally substituted alkyl group, an optionally substituted alkoxy group and the like are preferred.

Examples of the halogen atom include fluorine, chlorine, bromine atom and the like. Among these, fluorine is preferred.

Examples of the "alkyl group" of the "optionally substituted alkyl group" include, for example, a $C_{1-7}$ alkyl group (for example, methyl, ethyl, propyl, isopropyl, butyl, isobutyl, sec-butyl, tert-butyl, pentyl, hexyl, heptyl and the like). As the "substituent" of the "optionally substituted alkyl group", for example, a halogen atom, a hydroxy group, a $C_{1-6}$ alkoxy group (for example, methoxy, ethoxy, propoxy, butoxy and the like), a $C_{1-6}$ alkoxy-carbonyl group (for example, methoxycarbonyl, ethoxycarbonyl, propoxycarbonyl and the like), a carbamoyl group and the like can be exemplified, and the number of these substituents may be about 1 to 3. When the number of substituent is 2 or more, each substituents may be the same or different.

Examples of the "alkoxy group" of the "optionally substituted alkoxy group" include, for example, a $C_{1-6}$ alkoxy group (for example, methoxy, ethoxy, propoxy, isopropoxy, butoxy, isobutoxy, pentoxy and the like) and the like. Examples of the "substituent" of the "optionally substituted alkoxy group" are exemplified by those for the above-mentioned "substituent" of the "optionally substituted alkyl group", and the same goes for the number of the substituents.

Examples of the "aryl group" include, for example, a $C_{6-14}$ aryl group (for example, phenyl, 1-naphthyl, 2-naphthyl, biphenyl, 2-anthryl and the like) and the like.

Examples of the "aryloxy group" include, for example, a $C_{6-14}$ aryloxy group (for example, phenyloxy, 1-naphthyloxy, 2-naphthyloxy and the like) and the like.

Examples of the "acyl group" include, for example, a formyl, an alkylcarbonyl, an alkoxycarbonyl, a carbamoyl, an alkylcarbamoyl, an alkylsulfinyl, an alkylsulfonyl and the like.

Examples of the "alkylcarbonyl group" include, a $C_{1-6}$ alkyl-carbonyl group (for example, acetyl, propionyl and the like) and the like.

Examples of the "alkoxycarbonyl group" include, for example, a $C_{1-6}$ alkoxy-carbonyl group (for example, methoxycarbonyl, ethoxycarbonyl, propoxycarbonyl, butoxycarbonyl and the like) and the like.

Examples of the "alkylcarbamoyl group" include, a N—$C_{1-6}$ alkyl-carbamoyl group (for example, methylcarbamoyl, ethylcarbamoyl and the like), a N,N-di $C_{1-6}$ alkyl-carbamoyl group (for example, N,N-dimethylcarbamoyl, N,N-diethylcarbamoyl and the like), and the like.

Examples of the "alkylsulfinyl group" include, for example, a $C_{1-6}$ alkylsulfinyl group (for example, methylsulfinyl, ethylsulfinyl, propylsulfinyl, isopropylsulfinyl and the like).

Examples of the "alkylsulfonyl group" include, for example, a $C_{1-6}$ alkylsulfonyl group (for example, methylsulfonyl, ethylsulfonyl, propylsulfonyl, isopropylsulfonyl and the like).

Examples of the "acyloxy group" include, for example, an alkylcarbonyloxy group, an alkoxycarbonyloxy group, a carbamoyloxy group, an alkylcarbamoyloxy group, an alkylsulfinyloxy group, an alkylsulfonyloxy group and the like.

Examples of the "alkylcarbonyloxy group" include a $C_{1-6}$ alkyl-carbonyloxy group (for example, acetyloxy, propionyloxy and the like) and the like.

Examples of the "alkoxycarbonyloxy group" include, for example, a $C_{1-6}$ alkoxy-carbonyloxy group (for example, methoxycarbonyloxy, ethoxycarbonyloxy, propoxycarbonyloxy, butoxycarbonyloxy and the like) and the like.

Examples of the "alkylcarbamoyloxy group" include a $C_{1-6}$ alkyl-carbamoyloxy group (for example, methylcarbamoyloxy, ethylcarbamoyloxy and the like) and the like.

Examples of the "alkylsulfinyloxy group" include, for example, a $C_{1-7}$ alkylsulfinyloxy group (for example, methylsulfinyloxy, ethylsulfinyloxy, propylsulfinyloxy, isopropylsulfinyloxy and the like).

Examples of the "alkylsulfonyloxy group" include, for example, a $C_{1-7}$ alkylsulfonyloxy group (for example, methylsulfonyloxy, ethylsulfonyloxy, propylsulfonyloxy, isopropylsulfonyloxy and the like).

Examples of the "5- to 10-membered heterocyclic group" include, for example, a 5- to 10-membered (preferably 5- or 6-membered) heterocyclic group having one or more (for example, one to three) hetero atoms selected from a nitrogen atom, a sulfur atom and an oxygen atom in addition to a carbon atom. Specific examples thereof include 2- or 3-thienyl group, 2-, 3- or 4-pyridyl group, 2- or 3-furyl group, 1-, 2- or 3-pyrrolyl group, 2-, 3-, 4-, 5- or 8-quinolyl group, 1-, 3-, 4- or 5-isoquinolyl group, 1-, 2- or 3-indolyl group. Among these, 5- or 6-membered heterocyclic groups such as 1-, 2- or 3-pyrrolyl group are preferred.

Ring A is preferably a benzene ring which may have 1 or 2 substituents selected from a halogen atom, an optionally halogenated $C_{1-4}$ alkyl group, an optionally halogenated $C_{1-4}$ alkoxy group and 5- or 6-membered heterocyclic group.

Examples of the "aralkyl group" of the "optionally substituted aralkyl group" represented by $R^1$ include, for example, a $C_{7-16}$ aralkyl group (for example, $C_{6-10}$), aryl $C_{1-6}$ alkyl group such as benzyl, phenethyl and the like) and the like. Examples of the "substituent" of the "optionally substituted aralkyl group" include the same groups as those exemplified with respect to the "substituent" of the above-mentioned "optionally substituted alkyl group", and the number of the substituents is about 1 to 4. When the number of the substituents is 2 or more, each substituents may be the same or different.

Examples of the "acyl group" represented by $R^1$ include, for example, the "acyl group" exemplified as the substituent of the above-mentioned ring A.

Examples of the "acyloxy group" represented by $R^3$ include, for example, the "acyloxy group" exemplified as the substituent of the above-mentioned ring A.

The preferable $R^1$ is a hydrogen atom.

Examples of the "optionally substituted alkyl group" represented by $R^2$, $R^3$ or $R^4$ include the "optionally substituted alkyl group" exemplified as the substituent of the above-mentioned ring A.

Examples of the "optionally substituted alkoxy group" represented by $R^2$, $R^3$ or $R^4$ include the "optionally substituted alkoxy group" exemplified as the substituent of the above-mentioned ring A.

Examples of the "optionally substituted amino group" represented by $R^2$, $R^3$ or $R^4$ include, for example, an amino group, a mono-$C_{1-6}$ alkylamino group (for example, methylamino, ethylamino and the like), a mono-$C_{6-14}$ arylamino group (for example, phenylamino, 1-naphthylamino, 2-naphthylamino and the like), a di-$C_{1-6}$ alkylamino group (for example, dimethylamino, diethylamino and the like), a di-$C_{6-14}$ arylamino group (for example, diphenylamino and the like) and the like.

The preferable $R^2$ is a $C_{1-6}$ alkyl group, a $C_{1-6}$ alkoxy group, a $C_{1-6}$ alkoxy-$C_{1-6}$ alkoxy group and a di-$C_{1-6}$ alkylamino group. The more preferable $R^2$ is a $C_{1-3}$ alkyl group or a $C_{1-3}$ alkoxy group.

The preferable $R^3$ is a hydrogen atom, a $C_{1-6}$ alkoxy-$C_{1-6}$ alkoxy group or an optionally halogenated $C_{1-6}$ alkoxy group. The more preferable $R^3$ is a $C_{1-3}$ alkoxy group which may be halogenated or may be substituted with a $C_{1-3}$ alkoxy group.

The preferable $R^4$ is a hydrogen atom or a $C_{1-6}$ alkyl group. The more preferable $R^4$ is a hydrogen atom or a $C_{1-3}$ alkyl group (in particular, a hydrogen atom).

The preferable Y is a nitrogen atom.

Specific examples of compound (I') include the following compounds.

2-[[[3-methyl-4-(2,2,2-trifluoroethoxy)-2-pyridinyl]methyl]sulfinyl]-1H-benzimidazole, 2-[[(3,5-dimethyl-4-methoxy-2-pyridinyl)methyl]sulfinyl]-5-methoxy-1H-benzimidazole, 2-[[[4-(3-methoxypropoxy)-3-methyl-2-pyridinyl]methyl]sulfinyl]-1H-benzimidazole sodium salt, 5-difluoromethoxy-2-[[(3,4-dimethoxy-2-pyridinyl)methyl]sulfinyl]-1H-benzimidazole, and an optically active isomer thereof.

Among these compounds, lansoprazole, namely, 2-[[[3-methyl-4-(2,2,2-trifluoroethoxy)-2-pyridinyl]methyl]sulfinyl]-1H-benzimidazole and an optically active isomer thereof are preferred in particular.

Further, the above-mentioned compound (I') may be a racemic compound or an optically active isomer such as R-isomer and S-isomer represented by the above-mentioned formula (I). For example, the optically active isomers such as (R)-2-[[3-methyl-4-(2,2,2-trifluoroethoxy)-2-pyridinyl]methyl]sulfinyl]-1H-benzimidazole (hereinafter, sometimes referred to as lansoprazole R-isomer) and (S)-2-[[[3-methyl-4-(2,2,2-trifluoroethoxy)-2-pyridinyl]methyl]sulfinyl]-1H-benzimidazole (hereinafter, sometimes referred to as lansoprazole S-isomer) are preferred, and in particular, an optically active R-isomer is suitable for the present invention. Further, since lansoprazole, lansoprazole R-isomer and lansoprazole S-isomer and the like are not only stabilized by making into a dosage form itself but also more stabilized by blending a non-toxic salt, preferably a basic inorganic salt, and further providing an intermediate layer, they can be used in the form of amorphous solid, which may be contaminated with crystalline. In the present invention, the amorphous benzimidazole compound means a benzimidazole compound containing more amorphous form than crystalline form, usually, about 60% or more of the total.

The salt of compound (I') is preferably a pharmacologically acceptable salt, and for example, a salt with an inorganic base, a salt with an organic base, a salt with a basic amino acid and the like are exemplified.

Preferred examples of the salt with an inorganic base include, for example, alkali metal salts such as sodium salt and potassium salt; alkaline earth metal salts such as calcium salt and magnesium salt; ammonium salt and the like.

Preferred examples of the salt with an organic base include, for example, salts with an alkylamine (trimethylamine, triethylamine and the like), a heterocyclic amine (pyridine, picoline and the like), an alkanolamine (ethanolamine, diethanolamine, triethanolamine and the like), dicyclohexylamine, N,N'-dibenzylethylenediamine and the like.

Preferred examples of the salt with a basic amino acid include, for example, salts with arginine, lysine, ornithine and the like.

Among these salts, an alkali metal salt and an alkaline earth metal salt are preferred. In particular, a sodium salt is preferred.

The compound (I') and a salt thereof can be produced by methods known per se, and are produced by methods disclosed in, for example, JP-A 61-50978, U.S. Pat. No. 4,628,098, JP-A 10-195068, WO 98/21201, JP-A 52-62275, JP-A 54-141783 and the like, or analogous methods thereto. Further, the optically active isomer (I) or a salt thereof can be obtained by optical resolution methods (a fractional recrystallization method, a chiral column method, a diastereomer method, a method using microorganism or enzyme, and the like) and an asymmetric oxidation method, etc. In addition, lansoprazole R-isomer can be produced according to production methods described in, for example, WO 00-78745, WO 01/83473, WO 02/44167 and the like. Lansoprazole S-isomer can be also produced according to the production method described in WO 01/02389. Further, an amorphous lansoprazole or an optically active isomer thereof can be produced by preserving or heating hydrated crystals of lansoprazole or an optically active isomer thereof (preferably hydrate of lansoprazole, more preferably lansoprazole 0.5 hydrate or lansoprazole 1.5 hydrate) at about 20 to about 100° C. (preferably about 40 to about 80° C., more preferably about 50 to about 70° C.). In addition, heating may be carried out under reduced pressure or ventilation for drying, or heating alone may be simply performed.

Although the blending amount of benzimidazole compound having a PPI activity used in the present invention (hereinafter occasionally abbreviated as PPI) differs depending on the kind of active ingredient and the dose, the amount is, in the case of intestine disintegrative dosage form, about 1 h by weight to 100% by weight, preferably about 5% by weight to 50% by weight based on the total amount of solid dosage form of the present invention. According to the present invention, a dosage form containing higher amount of an active ingredient can be prepared, and in the case of such dosage form containing an active ingredient with a higher content, PPI may be contained with a ratio of about 12% by weight to about 40% by weight, preferably about 12% by weight to about 20% by weight, more preferably about 14% by weight to about 20% by weight. When the benzimidazole compound having PPI activity is lansoprazole or an optically active isomer thereof, a higher content of about 14% by weight to about 20% by weight is feasible. In the case of the stomach disintegrative dosage form, the blending amount is 0.001 to 0.3 parts by weight, preferably 0.002 to 0.2 parts by weight based on 1 part by weight of the solid dosage form of the present invention.

Examples of the non-toxic base used in the present invention are basic inorganic salts and organic bases. Any non-toxic bases can be used as long as 1% aqueous solution or suspension thereof shows a basic pH (pH 7 or more), and preferred are those showing a pH of 8.0 or more at 25° C. Especially, such basic inorganic salt is preferred. Preferred examples of the basic inorganic salts are a basic inorganic salt of sodium, potassium, magnesium and calcium. Preferably, a basic inorganic salt of magnesium or calcium is exemplified.

Examples of the basic inorganic salt of sodium are sodium carbonate, sodium hydrogen carbonate, sodium hydroxide and the like.

Examples of the basic inorganic salt of potassium are potassium carbonate, potassium hydrogen carbonate, potassium hydroxide and the like.

Examples of the basic inorganic salt of magnesium are heavy magnesium carbonate, magnesium carbonate, magnesium oxide, magnesium hydroxide, magnesium metasilicate aluminate, magnesium silicate, magnesium aluminate, synthetic Hydrotalcite [$Mg_6Al_2(OH)_{16}.CO_3.4H_2O$], and aluminum hydroxide.magnesium [$2.5MgO.Al_2O_3.xH_2O$], preferably, heavy magnesium carbonate, magnesium carbonate, magnesium oxide, magnesium hydroxide and the like.

Examples of the basic inorganic salt of calcium include precipitated calcium carbonate, calcium hydroxide and the like.

As a preferred basic inorganic salt, magnesium carbonate, calcium carbonate, and the like are exemplified.

The basic inorganic salt can be combined one kind thereof, or two kinds or more.

Examples of the organic base include, for example, an alkylamine (trimethylamine, triethylamine and the like), a heterocyclic amine (pyridine, picoline and the like), an alkanolamine (ethanolamine, diethanolamine, triethanolamine and the like), dicyclohexylamine, N,N'-dibenzylethylenediamine and a basic amino acid (arginine, lysine, ornithine and the like) and the like.

When a basic inorganic salt is blended, the blending amount is about 0.1 to about 20 parts by weight, preferably about 0.2 to about 10 parts by weight, more preferably about 0.2 to about 7 parts by weight based on 1 part by weight of PPI in the case of intestine disintegrative dosage form. In the above-mentioned dosage form containing higher amount of PPI, it is possible to blend with a ratio of about 0.2 to about 7% by weight, preferably about 0.2 to about 3% by weight, more preferably about 0.2 to about 1% by weight. In particular, in the case of dosage form containing higher amount of PPI which is lansoprazole or an optically active isomer thereof, it is preferred to blend the basic inorganic salt (preferably a basic inorganic salt of magnesium or calcium, more preferably magnesium carbonate, magnesium oxide) with a ratio of about 0.2 to about 1 part by weight, preferably about 0.2 to about 0.4 parts by weight based on 1 part by weight of PPI. As shown in the compatibility test mentioned below, it was found out that the degradation and discoloration of amorphous benzimidazole compounds which is extremely unstable alone are unexpectedly suppressed by making into a solid dosage form such as granules with concomitance of a base, in particular basic inorganic salt, more preferably magnesium carbonate, calcium carbonate, magnesium oxide, magnesium hydroxide, etc., if necessary, together with some excipients used for other pharmaceutical dosage forms, and therefore amorphous benzimidazole compounds can be used as a medicine. Particularly in the case of dosage form containing lansoprazole or an optically active isomer thereof with a higher content, it is preferred to blend a basic inorganic salt of magnesium or calcium, more preferably magnesium carbonate or magnesium oxide.

In the case of stomach disintegrative dosage form, in order to prevent a degradation of active ingredient due to the exposure to gastric acid, the basic inorganic salts are blended with suitable amount that they are quickly dissolved and neutralize gastric acid simultaneously with disintegration of solid dosage form in stomach, preferably, prior to dissolution of an active ingredient. Although the blending amount of each basic inorganic salt differs depending on the gastric acid-neutralizing ability, the basic inorganic salt (preferably magnesium oxide, magnesium hydroxide, or concomitant use of magnesium oxide and magnesium hydroxide) is generally blended with a ratio of about 0.05 to 2000 parts by weight, preferably about 0.1 to 1000 parts by weight, more preferably about 0.1 to 800 parts by weight relative to 1 part by weight of acid-labile active ingredient. For example, the blending amount of the basic inorganic salt is about 0.1 to 1500 parts by weight, preferably about 0.5 to 800 parts by weight, more preferably about 0.1 to 400 parts by weight relative to 1 part by weight of benzimidazole compound. In the case of benzimidazole compound as the active ingredient, although the pH in stomach usually increases simultaneously with initiation of dosing, the basic inorganic salt is preferably blended with suitable amount that the pH in stomach having a usual pH range increases to 4 or more within about 60 minutes, preferably about 40 minutes after administration.

Since the benzimidazole compound having a PPI activity has a slightly water soluble property and is unstable in acid condition, it is preferred to make it into an enteric dosage form with enteric coating layer. The enteric coating layer is not dissolved in stomach wherein pH is low and water content is comparatively rich, but is dissolved in small intestine wherein water content is poor and pH is high, after that, the benzimidazole compound is dissolved and absorbed. That is, since it is necessary that the composition containing benzimidazole compound can be disintegrated quickly in small intestine, granules or fine granules having large surface area and easy to disintegrate or dissolve quickly is preferred. If desired, these granules or fine granules may be formulated as tablets, or capsules by filling in capsules.

As a more preferred embodiment, although the blending amount of benzimidazole compound having a PPI activity as represented by lansoprazole, lansoprazole R-isomer and lansoprazole S-isomer can be changed appropriately depending on compounds and the dosage form, a "granules with average particle diameter of about 600 µm or more, which contains about 12% by weight to about 40% by weight of benzimidazole compound having a PPI activity based on the total amount of the granule and is blended with a basic inorganic salt as a stabilizer" is preferable to prepare a higher-content dosage form which is suitable for once-daily administration dosage form wherein unit dose is, for example, 40 mg to 90 mg, preferably 40 mg to 60 mg. When the diameter of granules is small, it becomes difficult to increase the content of benzimidazole compound since the surface area becomes larger, which requires a larger amount of enteric coat. Namely, the dosage form having a high content can be produced by setting the diameter of granules at least about 600 µm or more and thereby reducing the amount of enteric coat. In order to provide such a high drug content dosage form, it is preferred to prepare granules whose average diameter of granules is about 600 µm to about 2500 µm. The more preferable average diameter of granules is about 1000 µm to about 2000 µm. The granules may contain particles with about 400 µm to about 3000 µm of particle diameter, preferably about 500 µm to about 2500 µm of particle diameter in so far as their average particle diameter, as a whole, is within the above-mentioned range.

The particle diameter is measured according to a sieving method (Powder—Theory and Application—, page 475, 1979, Maruzen), and the average particle diameter is calculated based on the mean value of corresponding sieve mesh and the weight distribution. That is, the arithmetic average is calculated based on the product of mean value and each weight.

In the present invention, a known granulation method can be applied to prepare the solid dosage form in the form of granules as mentioned above. A rotary granulation method (e.g. centrifugal Fluid-bed granulation method), a fluidized granulation method, an agitation granulation method (e.g. agitator fluidized granulation method) and the like are included as the example of granulation method. Among them, a rotary granulation method and an agitation granulation method (agitator fluidized granulation method) are preferred.

CF granulator manufactured by Freund industrial Co., Ltd., and the like are included as operative examples of the rotary granulation method. Spiral Flow manufactured by Freund Industrial Co., Ltd., Multiplex manufactured by Powrex Co., Ltd., New-Marume manufactured by Fuji Paudal Co., Ltd., or the like are included operative examples of the agitator fluidized granulation method. A method for spraying a binder solution can be appropriately selected depending on the kind of granulator, for example, any of a top spraying method, a bottom spraying method, a tangential spraying method, and the like can be used.

In the case of intestine disintegrative dosage form, the granules of the present invention is preferably prepared as granules having active ingredients layer containing an active ingredient, an intermediate coating layer formed on said active ingredient layer, and an enteric coating layer or controlled release coating layer formed on said intermediate coating layer.

In order to obtain granules having a high sphericity and narrow particle size distribution, the granules of the present invention is preferred to form the active ingredient layer by coating with the benzimidazole compound on the core particles composed of one or more materials selected from sucrose, starch, lactose and crystalline cellulose. For example, granules having a core can be prepared according to the method described in JP-A 63-301816. The above mentioned granules can be prepared by a method of coating a dusting powder containing the benzimidazole compound having antiulcer activity, a basic metal salt, an excipient, a disintegrant and the like on the core sugar particles with spraying a binder solution of hydroxypropylcellulose and the like. As said core particles, for example, Nonpareil prepared by coating sucrose (75 parts by weight) with corn starch (25 parts by weight) according to a method known per se, a spherical core granule using crystalline cellulose and the like are exemplified. Alternatively, core granules per se may be an active ingredient which becomes the above active ingredient layer. An average particle size of the core granules is generally 14 to 80 mesh.

As the core particles, spherically granulated products made of sucrose and starch, spherically granulated products made of crystalline cellulose, spherically granulated products made of crystalline cellulose and lactose and the like are exemplified.

It is desirable that cores are as uniformly spherical as possible in order to minimize the variations of coating.

The ratio of coating layer relative to the core particles can be selected from within such a range that the dissolution profiles of the benzimidazole compound and a particle size of the granules can be controlled. For example, the ratio of coating layer relative to the core particles is usually about 0.2 part by weight to about 5 parts by weight based on 1 part by weight of core particle, and preferably about 0.1 part by weight to about 5 parts by weight.

The coating layer which coats the active ingredients layer may be composed of plural layers. The plural layers can contain various coating layers such as controlled release coating layer and undercoating layer in addition to intermediate coating layer and enteric coating layer without active ingredient. A particular combination of these coating layers may be appropriately selected.

Since the amorphous benzimidazole compound having a PPI activity is especially unstable, it is preferable from the viewpoint of improving stability of the active ingredients to make an intermediate coating layer between the active ingredients layer containing the amorphous benzimidazole compound and the enteric coating layer to block direct contact between the two layers because the component of enteric coating layer is an acidic substance, when enteric coated granules are prepared.

Such an intermediate coating layer may be a coating layer which can prevent direct contact between the benzimidazole compound as an active ingredient and an enteric coating layer, and the amount and material of the coating layer are not limited in so far as such an objective is achieved. For example, there is a layer in which a saccharide such as sucrose [refined white sugar (pulverized (powdered sugar) or not pulverized), etc.], starch sugar such as corn starch, lactose, honey, sugar alcohol (D-mannitol, erythritol, etc.), etc. is appropriately formulated into a polymer base such as low-substituted hydroxypropylcellulose, hydroxypropylcellulose, hydroxypropylmethylcellulose (e.g. TC-5, etc.), polyvinylpyrrolidone, polyvinyl alcohol, methylcellulose, hydroxyethylmethylcellulose and the like. In addition, excipients (e.g. masking agent (titanium oxide, etc.), and an antistatic agent (titanium oxide, talc, etc.)), which are added for preparing a dosage form as needed, may be added to the intermediate coating layer appropriately as described hereinafter.

The amount of the intermediate coating layer is usually about 0.02 part by weight to about 1.5 parts by weight, preferably about 0.05 part by weight to about 1 part by weight based on 1 part by weight of the granules containing, for example, benzimidazole compound. The coating can be performed according to a conventional method. For example, preferably, these intermediate coating layer components are diluted with purified water and sprayed as a liquid for coating. At this time, it is preferable to perform coating while spraying a binder agent of hydroxypropylcellulose or the like.

The "enteric coating layer" to be used for coating the granules in the present invention is dissolved at about pH 5.5 and initiate a release of active ingredient. The materials which constitute the enteric coating layer, for example, include aqueous enteric polymer bases such as cellulose acetate phthalate (CAP), hydroxypropylmethylcellulose phthalate, hydroxymethylcellulose acetate succinate, methacrylic acid copolymer, carboxymethylethylcellulose, shellac and the like, sustained-release bases such as ethyl acrylate-methacrylic acid copolymer and the like, and plasticizers such as water-soluble polymer, triethyl citrate, polyethylene glycol, acetylated monoglyceride, triacetin, castor oil and the like. These materials can be used alone or in combination of two or more thereof.

The enteric coating layer is an enteric polymer base, preferably an aqueous enteric methacrylic acid copolymer.

The coating amount of the enteric coating layer is about 10% by weight to about 70% by weight, preferably about 10% by weight to about 50% by weight, more preferably about 15% by weight to about 30% by weight based on the total amount of the granules before coating of the enteric coating.

The solid dosage form, inter alia, granules of the present invention may be prepared as a solid dosage form which shows a prolonged drug action by forming a "controlled release coating layer". Examples of such "controlled release coating layer" include a coating layer which is dissolved at a different pH range from that for a usual enteric coat (for example, pH 6 or above, preferably 6.5 or above), that is, a layer which releases a active ingredient pH-dependently, a diffusion-controlled coating layer whose layer itself is not dissolved and which releases a active ingredient through pores which are formed in the coating layer, and the like. Herein, the "pH-dependently" means that an active ingredient is released under circumstances of more than a certain pH value.

As a controlled release coating material for controlling the release of medical active ingredient pH-dependently, hydroxypropyl methylcellulose phthalate (HP-55, HP-50, manufactured by Shin-Etsu Chemical Co., Ltd.), cellulose acetate phthalate, carboxymethylethylcellulose (CMEC, manufactured by Freund Industrial Co., Ltd.), methacrylic acid-methyl methacrylate copolymer (Eudragit L100, manufactured by Rohm Co.), methacrylic acid-ethyl acrylate copolymer (Eudragit L100-55, Eudragit L30D-55, manufactured by Rohm Co.), hydroxypropyl cellulose acetate succinate (HP-MCAS manufactured by Shin-Etsu Chemical Co., Ltd.), polyvinyl acetate phthalate and shellac are used. These may be used alone to coat or at least 2 kinds or more of the polymers may be used to coat in combination, or at least 2 kinds or more of the polymers may be used to coat sequentially. It is desirable that the coating material is used alone or, if necessary, in combination in order that the polymer is dissolved preferably at pH of 6.0 or above, more preferably at a pH of 6.5 or above, and further more preferably at a pH of 6.75 or above.

Further, plasticizers such as polyethylene glycol, dibutyl sebacate, diethyl phthalate, triacetin and triethyl citrate, stabilizers and the like may be used for coating, if necessary. The amount of coating material is preferably 5% to 100% based on the core particles.

In addition, the diffusion-controlled coating layer which controls the release of active ingredients by diffusion can be formed by coating granules with a mixed solution prepared by mixing a material such as aminoalkyl methacrylate copolymer (Eudragit RS, RL, manufactured by Rohm Co.), ethyl, acrylate-methyl methacrylate copolymer (Eudragit NE30D manufactured by Rohm Co.), ethyl cellulose and the like with a hydrophilic pore forming substance such as HPMC, HPC, carboxyvinyl polymer, polyethylene glycol 6000, lactose, mannitol and organic acid at a fixed ratio.

Further, additives for preparing dosage forms such as excipients (for example, glucose, fructose, lactose, sucrose, D-mannitol, erythritol, multitol, trehalose, sorbitol, corn starch, potato starch, wheat starch, rice starch, crystalline cellulose, silicic acid anhydride, calcium metaphosphorate, sedimented calcium carbonate, calcium silicate, and the like), binders (for example, hydroxypropyl cellulose, hydroxypropyl methylcellulose, polyvinyl pyrrolidone, methyl cellulose, polyvinyl alcohol, carboxymethyl cellulose sodium, partially α-conformation starch, α-conformation starch, sodium alginate, pullulan, gum arabic powder, gelatin and the like), disintegrants (for example, low substituted hydroxypropyl cellulose, carmelose, carmelose calcium, carboxymethylstarch sodium, cross carmelose sodium, crosspovidon, hydroxypropylstarch and the like), flavoring agents (for example, citric acid, ascorbic acid, tartaric acid, malic acid, aspartame, acesulfam potassium, thaumatin, saccharin sodium, glycylrrhizin dipotassium, sodium glutamate, sodium 5'-inosinate, sodium 5'-guanylate and the like), surfactants (for example, polysolvate (polysolvate 80 and the like), polyoxyethylene-polyoxypropylene copolymer, sodium laurylsulfate and the like), perfumes (for example, lemon oil, orange oil, menthol, peppermint oil and the like), lubricants (for example, magnesium stearate, sucrose fatty acid ester, sodium stearylfumarate, stearic acid, talc, polyethylene glycol and the like), colorants (for example, titanium oxide, edible Yellow No. 5 (FD&C Yellow No. 5), edible Blue No. 2 (FD&C Blue No. 2), iron (III) oxide, yellow iron (III) oxide, and the like), antioxidants (for example, sodium ascorbate, L-cysteine, sodium bisulfate, and the like), masking agents (for example, titanium oxide and the like), and antistatic agents (for example, talc, titanium oxide and the like) can be used.

Although the particle diameter of raw materials used here are not particularly limited, a preferred particle diameter is about 500 μm or less from the viewpoint of productivity and dosing.

As the solid dosage form of the present invention, granules, capsules, tablets, effervescent dosage forms, suspensions or the like can also be used. As mentioned above, in case of capsules and tablets, granules or fine granules are prepared in advance for the purpose of improving stability and the like, with which may be formulated into the tablets or capsules.

From a viewpoint of easy handling, etc., capsules and tablets are preferred. As capsules, gelatin capsules, HPMC capsules, pullulan capsules and the like may be used. When used as capsules, size No. 3 to No. 5 capsules are preferable for easy administration. For example, in case of a capsule filled with granules containing an amorphous lansoprazole or an optically active isomer thereof, preferably, granules having an average particle diameter of about 1000 μm to about 2000 μm are prepared by coating an intermediate layer on a active ingredient layer, which contains lansoprazole or optically active isomer thereof in an amount of about 14% by weight to about 20% by weight based on the total granules and a basic salt of magnesium and/or calcium in an amount of about 0.2 part by weight to about 0.4 part by weight based on 1 part by weight of lansoprazole or optically active isomer thereof, and then coating an enteric layer thereon, and the granules are filled into a capsule. As a capsule containing 30 mg of lansoprazole per capsule, conventional products are size No. 1 to No. 2 capsules, while size No. 3 to No. 5 stable capsules can be produced according to the present invention. In addition, in case of capsules containing 15 mg of lansoprazole per capsule in which the above granules are filled, it is possible to reduce the size to No. 4 to No. 5 capsules. Further, in case of a capsule containing 60 mg of optically active isomer of lansoprazole such as lansoprazole R-isomer, size No. 3 to No. 1 capsules is possible. Furthermore, in case of a capsule containing 40 mg, No. 4 to No. 2 capsules is possible and, in case of a capsule containing 30 mg, No. 5 to No. 3 capsules is possible.

In the solid dosage form of the present invention, since the benzimidazole compound having a PPI activity which is the principal ingredient has excellent antiulcer activity, gastric acid secretion inhibiting activity, mucosa protecting activity, anti-*Helicobacter pylori* activity and the like, and has low toxicity, they are useful for medicine. In this case, the granules of the present invention can be administered to a mammal (e.g. human, monkey, sheep, horse, dog, cat, rabbit, rat, mouse, etc.) orally for the purpose of treating and preventing peptic ulcers (e.g. gastric ulcer, duodenal ulcer, stomal ulcer, etc.), Zollinger-Ellison syndromes, gastritis, reflux esophagitis, symptomatic gastroesophageal reflux disease (symptomatic GERD)), NUD (non ulcer dyspepsia), stomach cancer (including stomach cancer accompanied with promotion of production of interleukin-1β due to genetic polymorphism of interleukin-1), gastric MALT lymphoma and the like, eradicating *Helicobacter pylori*, suppressing upper gastrointestinal hemorrhage due to peptic ulcers, acute stress ulcer and hemorrhagic gastritis, suppressing upper digestive tract hemorrhagic due to invasion stress (stress resulting from major operation requiring post-operative intensive management, and cerebrovascular disorder, head trauma, multiple organ failure and diffuse burn requiring intensive care), treating and preventing ulcers resulting from non-steroidal antiinflammatory medicaments; treating and preventing excess stomach acid and ulcer due to post-operation stress, and the like. For eradicating *Helicobacter pylori*, etc., the granules or capsule of the present invention may be used together with other active component(s) (e.g. 1 to 3 kinds of active component(s)).

Examples of the "other active component(s)" include anti-*Helicobacter pylori* active substances, antimicrobial agents such as imidazole compounds, quinolone compounds, etc. and bismuth salts. Inter alia, medicines comprising a combination of the granules or capsule of the present invention and an antimicrobial agent are preferred. Among them, a combination with anti-*Helicobacter pylori* active substances, or antimicrobial agents such as imidazole compounds and the like is preferred. Examples of the "anti-*Helicobacter pylori* active substances" include penicillin antibiotics (e.g. amoxicillin, benzylpenicillin, piperacillin, mecillinam, etc.), cephem antibiotics (e.g. cefixime, cefaclor, etc.), macrolide antibiotics (e.g. erythromycin antibiotics such as erythromycin, clarithromycin, etc.), tetracycline antibiotics (e.g. tetracycline, minocycline, streptomycin, etc.), aminoglycoside antibiotics (e.g. gentamycin, amikacin, etc.), imipenem and the like. Inter alia, penicillin antibiotics and macrolide antibiotics are preferred.

Examples of the "imidazole compounds" include metronidazole, miconazole, etc. Examples of the "bismuth salt" include bismuth acetate, bismuth citrate, etc. Antibacterial agents of "quinolone compounds" are also preferred, and examples thereof include ofloxacin, ciprofloxacin, etc. Inter alia, for eradicating *Helicobacter pylori*, it is preferred to use the granules or capsules of the present invention in combination with penicillin antibiotics (e.g. amoxicillin, etc.) and/or erythromycin antibiotics (e.g. clarithromycin etc.). In addition, the concomitant use with metronidazole is also preferred, and the concomitant use of three agents consisting of two agents selected from amoxicillin, clarithromycin and metronidazole, and an imidazole compound, in particular, lansoprazole or lansoprazole R-isomer has an excellent *Helicobacter pylori* eradicating action.

For example, in case of lansoprazole, in many cases, a conventional crystalline lansoprazole 15 mg-containing capsule is a product filled into a size No. 3 capsule, and a conventional 30 mg-containing capsule is a product filled into a size No. 1 capsule. However, according to the present invention, since the amounts of components except for the active ingredient can be reduced without deteriorating stability of the amorphous active ingredient and a dosage form, the size of a 15 mg-containing capsules can be reduced to No. 4 to No. 5 capsules, and the size of a 30 mg-containing capsules can be reduced to No. 3 to No. 5 capsules, respectively.

Further, even in a 60 mg-containing capsules, it is possible to use No. 1 to No. 3 capsules.

Furthermore, in case of an optically active isomer of lansoprazole, size No. 3 to No. 5 capsules, size No. 2 to No. 4 capsules and size No. 1 to No. 3 capsules can be used for 30 mg-, 40 mg- and 60 mg-containing capsules, respectively, size No. 1 to No. 3 capsules can be also used for 90 mg-containing capsules.

For example, because of a high content of an active component and easy administration, a capsule containing 60 mg of amorphous lansoprazole or lansoprazole R-isomer is suitable for treating, inter alia, acid hypersecretion symptom including Zollinger-Ellison syndromes.

A daily dosage varies depending on the degree of symptom, the age, sex and weight of subject, the administration time, interval, and the kind of principal or active ingredient, etc., and is not specifically limited. For example, when orally administered to an adult (60 kg) as an antiulcer agent, a dosage is about 0.5 to 1500 mg/day, preferably about 5 to 150 mg/day in terms of an active component. These dosage forms containing benzimidazole compounds may be administered once or by dividing into 2 to 3 times daily.

Further, stabilization in a package form may be also provided in order to improve the stability of the solid dosage form of the present invention at storage or transportation. For example, the stabilization of the solid dosage form containing the amorphous benzimidazole compound of the present invention can be improved by using package form such as package suppressing the permeation of oxygen, package replaced with gas (namely, package replaced with gas other than oxygen), vacuum package and package enclosed with a deoxidizer. Using these package forms, the stabilization is improved by reducing oxygen amount with which the solid dosage form is directly brought in contact. When a deoxidizer is enclosed, the pharmaceutical solid dosage form is packed with an oxygen permeating material, and then another packing may be carried out together with the package.

Regarding the benzimidazole compound having a PPI activity which is the principal drug of the present invention, conventionally both racemic compound and optically active isomers are usually used as crystals. Since the benzimidazole compound having a PPI activity is generally easy to crystallize, once it has been crystallized, thereafter it becomes difficult to synthesize as an amorphous form, though it was synthesized as an amorphous substance (non-crystalline form, same meaning as amorphous form) at the threshold of finding of the compound. Inter alia, although lansoprazole R-isomer was synthesized as an amorphous form at first, it becomes difficult to synthesize as an amorphous form after the success of crystallization (WO 00/78745 etc.). This is a general phenomenon, and once crystals have been given, it is usually not easy to synthesize an amorphous substance with the same method as ever. Namely, anhydrous lansoprazole R-isomer won't convert to amorphous form by heating directly, and when a solution containing lansoprazole is concentrated, an amorphous substance cannot be synthesized by a conventional method because nowadays anhydrous crystals or hydrated crystals crystallize since once they have been crystallized.

However, since an amorphous lansoprazole has such merits that it has a higher solubility relative to crystals and better absorbability, the present inventors have devoted themselves to research a process for producing amorphous lansoprazole, and unexpectedly found out a method for producing amorphous lansoprazole conveniently. That is, it is found out that an amorphous lansoprazole can be produced by maintaining hydrated crystals of lansoprazole R-isomer (preferably hydrate of lansoprazole R-isomer, more preferably 0.5 hydrate of lansoprazole R-isomer or 1.5 hydrate of lansoprazole R-isomer) at about 20° C. to about 100° C. or by heating, if necessary. Maintaining or heating under drying is preferred. The amorphous substance of lansoprazole R-isomer can be produced by heating, preferably at about 40° C. to about 80° C., more preferably at about 50° C. to about 70° C. In addition, heating may be carried out under reduced pressure combining with drying, or under ventilation. Alternatively, it is also effective to simply heat.

Hereinafter, the present invention will be illustrated in more detail by Examples and Experiments, but the present invention is not limited by them.

Production Example 1

Synthesis of Amorphous Lansoprazole R-Isomer

To a mixed solution of acetone (55 mL) and water (270 mL) was added dropwise a solution of crystals of lansoprazole R-isomer anhydride (powder X-ray diffraction chart is attached) (40 g) in acetone (180 mL) over about 10 minutes. Then water (340 mL) was added dropwise thereto over about 20 minutes, and resulting solution was stirred at 0 to 10° C. for about 1 hr. The precipitated crystals were collected by filtration, and washed with a mixed solution (90 mL) of acetone/water (1/5), followed by water (90 mL). The resulting wet crystals were dried at about 65° C. under reduced pressure for about 7 hrs to give amorphous lansoprazole R-isomer (amount: 38.4 g, yield: 96%). In addition, the crystals before drying under reduced pressure are 1.5 hydrate of lansoprazole R-isomer.
Elementary Analysis
  Calculated: C, 52.03; H, 3.82; N, 11.38, S, 8.68, F, 15.43, O, 8.66.
  Found: C, 51.77; H, 3.84; N, 11.39, S, 8.59, F, 1.5.48.

$^1$H-NMR (CDCl$_3$): 2.25 (3H, s), 4.39 (2H, q, J=7.3 Hz), 4.72 (1H, d, J=13.8 Hz), 4.85 (1H, d, J=13.8 Hz), 6.69 (1H, d), 7.31-7.80 (4H, m), 8.35 (1H, d), 11.5 (1H, br S)
powder X-ray diffraction: no specific peak was detected
chemical purity (area percent value): 98.3%
optical purity: 100% ee
moisture (KF method): 0.5%

Production Example 2

Synthesis of Amorphous Lansoprazole R-Isomer 1.5 Hydrate of lansoprazole R-isomer (10 g) was dried at about 60° C. under reduced pressure for about 8 hrs to give amorphous lansoprazole R-isomer (amount: 9.3 g, yield: 100%).
Elementary Analysis
  Calculated: C, 52.03; H, 3.82; N, 11.38, S, 8.68, F, 15.43, O, 8.66.
  Found: C, 52.17; H, 3.92; N, 11.23, S, 8.58, F, 15.40.
$^1$H-NMR (CDCl$_3$): 2.25 (3H, S), 4.39 (2H, q, J=7.8 Hz), 4.72 (1H, d, J=13.8 Hz), 4.85 (1H, d, J=13.8 Hz), 6.69 (1H, d), 7.31-7.80 (4H, m), 8.35 (1H, d), 11.5 (1H, br S)
powder X-ray: no specific peak was detected
chemical purity: 97.9% (area percent value)
optical purity: 99.8% ee
moisture (KF method): 0.7%

Production Example 3

Synthesis of Amorphous Lansoprazole R-Isomer 1.5 Hydrate of lansoprazole R-isomer (10 g) was dried at about 65° C. under ventilation for about 7 hrs to give amorphous lansoprazole R-isomer (amount: 9.3 g, yield: 100%).
Elementary Analysis
  Calculated: C, 52.03; H, 3.82; N, 11.38, S, 8.68, F, 15.43, O, 8.66.
  Found: C, 52.08; H, 3.90; N, 11.25, S, 8.56, F, 15.37.
$^1$H-NMR (CDCl$_3$): 2.25 (3H, S), 4.39 (2H, q, J=7.8 Hz), 4.72 (1H, d, J=13.8 Hz), 4.85 (1H, d, J=13.8 Hz), 6.69 (1H, d), 7.31-7.80 (4H, m), 8.35 (1H, d), 11.5 (1H, br S)
powder X-ray: no specific peak was detected
chemical purity: 98.4% (area percent value)
optical purity: 100% ee
moisture (KF method): 0.4%

Production Example 4

Synthesis of Amorphous Lansoprazole R-Isomer 1.5 Hydrate of lansoprazole R-isomer (10 g) was heated at about 65° C. for about 8 hrs to give amorphous lansoprazole R-isomer (amount: 9.3 g, yield: 100%).
Elementary Analysis
  Calculated: C, 52.03; H, 3.82; N, 11.38, S, 8.68, F, 15.43, O, 8.66.
  Found: C, 52.12; H, 3.74; N, 11.30, S, 8.74, F, 15.40.
$^1$H-NMR (CDCl$_3$): 2.25 (3H, S), 4.39 (2H, q, J=7.8 Hz), 4.72 (1H, d, J=13.8 Hz), 4.85 (1H, d, J=13.8 Hz), 6.69 (1H, d), 7.31-7.80 (4H, m), 8.35 (1H, d), 11.5 (1H, br S)
powder X-ray: no specific peak was detected
chemical purity: 97.6% (area percent value)
optical purity: 99.7% ee
moisture (KF method): 0.5%

Production Example 5

Synthesis of Amorphous Lansoprazole R-Isomer 0.5 Hydrate of lansoprazole R-isomer (10 g) was dried at about 70° C. under reduced pressure for about 6 hrs to give amorphous lansoprazole R-isomer (amount: 9.8 g, yield: 100%).
Elementary Analysis
  Calculated: C, 52.03; H, 3.82; N, 11.38, S, 8.68, F, 15.43, O, 8.66.
  Found: C, 51.98; H, 3.95; N, 11.30, S, 8.78, F, 15.35.
  $^1$H-NMR (CDCl$_3$): 2.25 (3H, S), 4.39 (2H, q, J=7.8 Hz), 4.72 (1H, d, J=13.8 Hz), 4.85 (1H, d, J=13.8 Hz), 6.69 (1H, d), 7.31-7.80 (4H, m), 8.35 (1H, d), 11.5 (1H, br S)
powder X-ray: no specific peak was detected
chemical purity: 98.0% (area percent value)
optical purity: 99.6% ee
moisture (KF method): 0.7%

Reference Example 1

Synthesis of 0.5 Hydrate of Lansoprazole R-Isomer

To a mixed solution of acetone (55 mL) and water (270 mL) was added dropwise a solution of crystals of lansoprazole R-isomer anhydride (refer to FIG. 1: powder X-ray diffraction chart) (40 g) in acetone (180 mL) over about 10 minutes. Then water (340 mL) was added dropwise to the solution over about 20 minutes, and the resulting solution was stirred at 0 to 10° C. for about 1 hr. The precipitated crystals were collected by filtration, and washed with a mixed solution (90 mL) of acetone/water (1/5), followed by water (90 mL). The resulting wet crystals were dried at about 30° C. under reduced pressure for about 7 hrs to give 0.5 hydrate of lansoprazole R-isomer (amount: 39.3 g, yield: 96%). In addition, the crystals before drying under reduced pressure are 1.5 hydrate of lansoprazole R-isomer.
Elementary Analysis
  Calculated: C, 50.79; H, 4.00; N, 11.11, S, 8.47, F, 15.06, O, 10.57.
  Found: C, 51.00; H, 3.92; N, 11.23, S, 8.65, F, 15.10.
  $^1$H-NMR (CDCl$_3$): 2.25 (3H, S), 4.39 (2H, q, J=7.8 Hz), 4.72 (1H, d, J=13.8 Hz), 4.85 (1H, d, J=13.8 Hz), 6.69 (1H, d), 7.31-7.80 (4H, m), 8.35 (1H, d), 11.5 (1H, br S)
powder X-ray diffraction: lattice spacing (d) 9.50, 8.73, 8.31, 5.57, 5.18, 4.80, 4.20
chemical purity: 99.6% (area percent value)
optical purity: 100%
moisture (KF method): 2.4%

Reference Example 2

Synthesis of 1.5 Hydrate of Lansoprazole R-Isomer

To a mixed solution of acetone (55 mL) and water (270 mL) was added dropwise a solution of crystals of lansoprazole R-isomer anhydride (refer to FIG. 1: powder X-ray diffraction chart) (40 g) in acetone (180 mL) over about 10 minutes. Then water (340 mL) was added dropwise to the solution over about 20 minutes, and the resulting solution was stirred at 0 to 1000 for about 1 hr. The precipitated crystals were collected by filtration, and washed with a mixed solution (90 mL) of acetone/water (1/5), followed by water (90 mL). The resulting wet crystals were dried at about 15° C. under reduced pressure for about 5 hrs to give 1.5 hydrate of lansoprazole R-isomer (amount: 41.6 g, yield: 97%). In addition, the crystals before drying under reduced pressure are 1.5 hydrate of lansoprazole R-isomer.
Elementary Analysis
  Calculated: C, 50.39; H, 4.05; N, 11.02, S, 8.41, F, 14.94, O, 11.19.
  Found: C, 50.50; H, 3.94; N, 11.32, S, 8.25, F, 14.73.
  $^1$H-NMR (CDCl$_3$): 2.25 (3H, S), 4.39 (2H, q, J=7.3 Hz), 4.72 (1H, d, J=13.8 Hz), 4.85 (1H, d, J=13.8 Hz), 6.69 (1H, d), 7.31-7.80 (4H, m), 8.35 (1H, d), 11.5 (1H, br S)
powder X-ray diffraction: lattice spacing (d) 8.91, 8.07, 6.62, 6.00, 5.92, 5.66, 5.04, 4.51
chemical purity: 99.6% (area percent value)
optical purity: 100%
moisture (KF method): 6.8%

Dosage Form Example 1

Composition is shown in Table 1. An amorphous lansoprazole R-isomer, magnesium carbonate, sucrose (pulverized sucrose), corn starch and low-substituted hydroxypropylcellulose were thoroughly mixed to obtain a dusting powder of active ingredient. In addition, sucrose (pulverized sucrose), corn starch and low-substituted hydroxypropylcellulose were thoroughly mixed to obtain a dusting powder for intermediate layer. Sucrose/starch spheres were placed in a centrifugal fluid-bed granulator (manufactured by Freund Industrial Co., Ltd., CF) and the above dusting powder of active ingredient and the dusting powder for intermediate layer were coated sequentially on the sucrose/starch spheres while spraying a hydroxypropyl cellulose solution (2%: w/w) to obtain spherical granules. Coating operation is carried out under the condition of rotor revolution speed: 300 rpm, coating solution spray rate: 1.8 g/min., spray air pressure: 0.2 kg/cm$^2$ and slit air pressure: 0.2 kg/cm$^2$. The obtained spherical granules were dried at 40° C. for 20 hrs under vacuum and passed through a round sieve to give granules of 710 μm-1420 μm.

An enteric coating solution was coated on the above granules using a fluidized granulation coating machine (manufactured by Powlex, LAB-1), which was dried as such, and passed through a round sieve to obtain enteric granules of 850 to 1420 μm. Coating operation is carried out under the condition of inlet air rate: 0.6 cm$^3$/min., inlet air temperature: 85° C., coating solution spray rate: 6 g/min., and spray air pressure: 1 kg/cm$^2$.

The obtained granules were mixed with talc and aerosil. And 150 mg (30 mg equivalent of lansoprazole R-isomer), 200 mg (40 mg equivalent of lansoprazole R-isomer) and 300 mg (60 mg equivalent of lansoprazole R-isomer) of the resultant mixed granules were filled in a size No. 4 capsule, No. 3 capsule and size No. 2 capsule, respectively.

Dosage Form Example 2

Composition is shown in Table 1. An amorphous lansoprazole R-isomer, magnesium carbonate, sucrose (pulverized sucrose) and low-substituted hydroxypropylcellulose were thoroughly mixed to obtain a dusting powder of active ingredient. In addition, sucrose (pulverized sucrose), low-substituted hydroxypropylcellulose and titanium oxide were thoroughly mixed to obtain a dusting powder for intermediate layer. Sucrose/starch spheres were placed in a centrifugal fluid-bed granulator (manufactured by Freund Industrial Co., Ltd., CF) and the above dusting powder of active ingredient and the dusting powder for intermediate layer were coated sequentially on the sucrose/starch spheres while spraying a hydroxypropyl cellulose solution (2%: w/w) to obtain spherical granules. Coating operation is carried out under the condition of rotor revolution speed: 300 rpm, coating solution spray rate: 1.8 g/min., spray air pressure: 0.2 kg/cm$^2$ and slit air pressure: 0.2 kg/cm$^2$. The obtained spherical granules were dried at 40° C. for 20 hrs under vacuum and passed through a round sieve to give granules of 710 μm-1420 μm.

An enteric coating solution was coated on the above granules using a fluidized granulation coating machine (manufactured by Powlex, LAB-1), which was dried as such, and passed through a round sieve to obtain enteric granules of 850 to 1420 μm. Coating operation is carried out under the condition of inlet air rate: 0.6 cm$^3$/min., inlet air temperature: 85° C., coating solution spray rate: 8 g/min., and spray air pressure: 1 kg/cm$^2$.

The obtained granules were mixed with talc and aerosil. And 150 mg (30 mg equivalent of lansoprazole R-isomer), 200 mg (40 mg equivalent of lansoprazole R-isomer) and 300 mg (60 mg equivalent of lansoprazole R-isomer) of the resultant mixed granules were filled in a size No. 4 capsule, No. 3 capsule and size No. 2 capsule, respectively.

Dosage Form Example 3

Composition is shown in Table 1. An amorphous lansoprazole R-isomer, magnesium carbonate, sucrose (pulverized sucrose), low-substituted hydroxypropylcellulose and titanium oxide were thoroughly mixed to obtain a dusting powder of active ingredient. Sucrose/starch spheres were placed in a centrifugal fluid-bed granulator (manufactured by Freund Industrial Co., Ltd., CF) and the above dusting powder of active ingredient was coated on the sucrose/starch spheres while spraying a hydroxypropyl cellulose solution (2%: w/w) to obtain spherical granules. Coating operation is carried out under the condition of rotor revolution speed: 300 rpm, coating solution spray rate: 1.8 g/min., spray air pressure: 0.2 kg/cm$^2$ and slit air pressure: 0.2 kg/cm$^2$. The resulting spherical granules were dried at 40° C. for 20 hrs under vacuum and passed through a round sieve to give granules of 710 μm-1420 μm.

An enteric coating solution was coated on the above granules using a fluidized granulation coating machine (manufactured by Powlex, LAB-1), which was dried as such, and passed through a round sieve to obtain enteric granules of 850 to 1420 μm. Coating operation is carried out under the condition of inlet air rate: 0.6 cm$^3$/min., inlet air temperature: 85° C., coating solution spray rate: 8 g/min., and spray air pressure: 1 kg/cm$^2$.

The obtained granules were mixed talc and aerosil. And 150 mg (30 mg equivalent of lansoprazole R-isomer), 200 mg (40 mg equivalent of lansoprazole R-isomer) and 300 mg (60 mg equivalent of lansoprazole R-isomer) of the resultant mixed granules were filled in a size No. 4 capsule, size No. 3 capsule and size No. 2 capsule, respectively.

TABLE 1

| Composition Table | | | |
|---|---|---|---|
| Composition in Granules 160 mg | | | |
|  | Dosage Form Example 1 | Dosage Form Example 2 | Dosage Form Example 3 |
| sucrose•starch spheres dusting powder of active ingredient | 50 mg | 50 mg | 50 mg |
| amorphous lansoprazole R-isomer | 40 mg | 40 mg | 40 mg |
| magnesium carbonate | 14 mg | 14 mg | 14 mg |
| sucrose (pulverized sucrose) | 26 mg | 26 mg | 36 mg |
| corn starch | 9 mg | 0 mg | 0 mg |
| low-substituted hydroxypropylcellulose | 10 mg | 10 mg | 12.5 mg |
| titanium oxide dusting powder for intermediate layer | 0 mg | 0 mg | 6.5 mg |
| sucrose (pulverized sucrose) | 5 mg | 10 mg |  |
| corn starch | 2.5 mg | 0 mg |  |
| low-substituted hydroxypropylcellulose | 2.5 mg | 2.5 mg |  |
| titanium oxide binder solution | 0 mg | 6.5 mg |  |
| hydroypropylcellulose | 1 mg | 1 mg | 1 mg |
| purified water | 49 μl | 49 μl | 49 μl |
| total | 160 mg | | |

Experiment

Stability Test of Amorphous Lansoprazole R-Isomer (1) 100 mg of amorphous lansoprazole R-isomer was weighed precisely under low humidity environment, and put in a transparent glass bottle. Subsequently, 100 mg of basic substance as a stabilizer of basic inorganic salt shown below was weighed precisely under low humidity environment, and placed in the bottle containing amorphous lansoprazole R-isomer. Then, the bottle was capped, and shaken slightly with hand to mix.

<Basic Substance>
[1] magnesium carbonate MgCO$_3$
[2] calcium carbonate CaCO$_3$
[3] magnesium oxide MgO
[4] magnesium hydroxide Mg (OH)$_2$
[5] no basic substance (2) The prepared samples were stored under the condition of 40° C./75% RH (open) for 5 days. Color tones were named and color codes were numbered based on International Color Manual so as to estimate the appearance change of samples everyday. At the end of experiment, the stability was judged by comparing the color tone with that of the sample stored at 5° C. as initial sample.

(3) As for the result of experiment, appearance changes are shown in Table 2. In addition, A represents amorphous lansoprazole R-isomer in Table 2.

TABLE 2

|  |  | Storage conditions | |
|---|---|---|---|
| basic substance | blending ratio (A/base) | initial (5° C. 5 days) | 40° C./75% RH 5 days |
| MgCO$_3$ | 1/1 | whity-greenish yellow | whity-greenish yellow (not changed) |
| CaCO$_3$ | 1/1 | slightly greenish yellow | pale greenish yellow (slightly changed) |
| MgO | 1/1 | whity-yellow | whity-yellow (not changed) |
| Mg(OH)$_2$ | 1/1 | whity-yellow | whity-yellow (not changed) |

TABLE 2-continued

| basic substance | blending ratio (A/base) | Storage conditions initial (5° C. 5 days) | 40° C./75% RH 5 days |
|---|---|---|---|
| No Addition | 1/0 | pale greenish yellow | pale yellow (changed) |

From the results of Table 2, it was confirmed that in the storing under 40° C./75% RH for 5 days, magnesium carbonate, calcium carbonate, magnesium oxide and magnesium hydroxide have a stabilization effect. That is, an effect of preventing appearance change is obtained by adding these basic inorganic salts.

INDUSTRIAL APPLICABILITY

According to the present invention, a stable solid dosage form can be prepared by blending a non-toxic base represented by a basic inorganic salt of magnesium, calcium, sodium and the like into a very unstable amorphous benzimidazole compound having proton pump inhibitor activity, or more preferably by forming an intermediate coating layer on the layer containing the active ingredient and further coating this with an enteric coating layer or a release-controlling coating layer.

Further, the present invention provides a novel process for producing an amorphous form of benzimidazole compound useful as PPI, which was once crystallized, inter alia, an amorphous form of optically active isomer, for example, amorphous lansoprazole R-isomer.

The invention claimed is:

1. A stable solid dosage form comprising a non-toxic base and an amorphous R-isomer of lansoprazole, or a salt thereof having a proton pump inhibitor (PPI) activity,
    wherein the non-toxic base is at least one selected from the group consisting of basic inorganic salts and organic bases,
    wherein the amorphous R-isomer of lansoprazole or salt thereof, contains 60% or more of an amorphous form.

2. The solid dosage form according to claim 1, wherein the non-toxic base is an inorganic salt of which 1% aqueous solution or 1% aqueous suspension shows a pH value of 8.0 or more at 25° C.

3. The solid dosage form according to claim 1, which has a coating layer.

4. The solid dosage form according to claim 3, wherein the coating layer contains an enteric coating layer.

5. The solid dosage form according to claim 3, wherein the coating layer contains a controlled release coating layer.

6. The solid dosage form according to claim 3, wherein the coating layer contains an intermediate coating layer formed on a layer containing the amorphous R-isomer of lansoprazole or salt thereof and a controlled release coating layer and/or enteric coating layer formed on said intermediate coating layer.

7. The solid dosage form according to claim 1, which further comprises an excipient.

8. The solid dosage form according to claim 1, which comprises further a basic inorganic salt stabilizer that is a carbonate of alkaline earth metal.

9. The solid dosage form according to claim 1, wherein the non-toxic base is one or more selected from a basic inorganic salt of sodium, a basic inorganic salt of potassium, a basic inorganic salt of magnesium, a basic inorganic salt of calcium, an alkylamine, a heterocyclic amine, an alkanolamine, dicyclohexylamine, N,N'-dibenzylethylenediamine and a basic amino acid.

10. The solid dosage form according to claim 1, wherein the non-toxic base is at least one selected from the group consisting of sodium carbonate, sodium hydrogen carbonate, sodium hydroxide, potassium carbonate, potassium hydrogen carbonate, potassium hydroxide, heavy magnesium carbonate, magnesium carbonate, magnesium oxide, magnesium hydroxide, magnesium metasilicate aluminate, magnesium silicate, magnesium aluminate, synthetic Hydrotalcite [$Mg_6Al_2(OH)_{16}.CO_3.4H_2O$], aluminum hydroxide magnesium [$2.5MgO\cdot AlO_3.xH_2O$], precipitated calcium carbonate and calcium hydroxide.

11. The solid dosage form according to claim 1, wherein the basic inorganic salt is included in an amount of about 0.1 to about 20 parts by weight of the amorphous R-isomer of lansoprazole, or the salt thereof.

12. The solid dosage form according to claim 1, wherein the dosage form is suitable for once-daily administration.

13. The solid dosage form according to claim 12, wherein a unit dose of the dosage form is 40 mg to 60 mg.

14. A capsule comprising granules or fine granules,
    wherein the granules or fine granules comprising a non-toxic base and an amorphous R-isomer of lansoprazole, or a salt thereof having a proton pump inhibitor (PPI) activity,
    wherein the non-toxic base is at least one selected from the group consisting of basic inorganic salts and organic bases,
    wherein the amorphous R-isomer of lansoprazole or salt thereof, contains 60% or more of an amorphous form.

15. The capsule according to claim 14, wherein the granules or fine granules comprise 30 mg equivalent of lansoprazole R-isomer.

16. The capsule according to claim 14, wherein the granules or fine granules comprise 60 mg equivalent of lansoprazole R-isomer.

17. The capsule according to claim 14, wherein the average diameter of the granules or fine granules is about 600 µm to about 2500 µm.

18. The capsule according to claim 14, wherein the average diameter of granules or fine granules is about 1000 µm to about 2000 µm.

19. The capsule according to claim 14, wherein the average diameter of granules or fine granules is about 400 µm to about 3000 µm of particle diameter.

20. The capsule according to claim 14, wherein the average diameter of granules or fine granules is about 500 µm to about 2500 µm of particle diameter.

21. The capsule according to claim 14, wherein the capsule is suitable for once-daily administration.

* * * * *